(12) United States Patent
Hung

(10) Patent No.: US 6,982,930 B1
(45) Date of Patent: Jan. 3, 2006

(54) WRISTWATCH WITH THE FUNCTION OF SENSING HEART PULSES

(76) Inventor: Chin-Yeh Hung, No.29-2, Cheng San, Lin 2, Ning Pu, Chang Pin Town, Taitung Hsien (TW)

( * ) Notice: Subject to any disclaimer, the term of this patent is extended or adjusted under 35 U.S.C. 154(b) by 0 days.

(21) Appl. No.: 10/898,945

(22) Filed: Jul. 27, 2004

(51) Int. Cl.
*G04B 47/00* (2006.01)
*A61B 5/00* (2006.01)

(52) U.S. Cl. .......................... 368/10; 600/500; 600/503
(58) Field of Classification Search ................. 368/10, 368/281, 278; 600/500–503
See application file for complete search history.

(56) References Cited

U.S. PATENT DOCUMENTS

| | | | | |
|---|---|---|---|---|
| 4,337,529 A | * | 6/1982 | Morokawa | 368/10 |
| 4,448,199 A | * | 5/1984 | Schmid | 600/393 |
| 4,450,843 A | * | 5/1984 | Barney et al. | 600/503 |
| 5,243,992 A | * | 9/1993 | Eckerle et al. | 600/503 |
| 5,471,983 A | * | 12/1995 | Magnus | 600/390 |
| 5,738,104 A | * | 4/1998 | Lo et al. | 600/521 |
| 5,787,054 A | * | 7/1998 | Yasukawa et al. | 368/204 |
| 5,795,300 A | * | 8/1998 | Bryars | 600/500 |
| 5,894,454 A | * | 4/1999 | Kondo | 368/11 |
| 6,238,354 B1 | * | 5/2001 | Alvarez | 600/549 |
| 6,529,754 B2 | * | 3/2003 | Kondo | 600/344 |

* cited by examiner

*Primary Examiner*—P. Austin Bradley
*Assistant Examiner*—Jeanne-Marguerite Goodwin
(74) *Attorney, Agent, or Firm*—Rosenberg, Klein & Lee

(57) ABSTRACT

A wristwatch with the function of sensing heart pulses having a watch housing on whose surface a liquid crystal display (LCD) is disposed. A voltage sensor is positioned within the watch housing for detecting the voltage frequency change during the blood circulation. The voltage sensor includes two electric terminals one of which is mounted on a bottom cover of the watch housing to permit a close contact with one hand wrist, and the other consists of two pieces of conductive rubber strips on the front surface of the insulated wristband for fingers of another hand to touch thereon. Both electric terminals are coupled by both hands while the detected voltage change frequency undergoes a static electric filtration by inductors and is transmitted to a filter shaping circuit for creating signals that are brought into a central processing unit to perform the processing and the calculating actions thereof. So, the processed result of the heart pulse rate is presented on the LCD.

3 Claims, 5 Drawing Sheets

WRISTWATCH WITH THE FUNCTION OF SENSING HEART PULSES

BACKGROUND OF THE INVENTION

1. Field of the Invention

The invention relates to a wristwatch with the function of sensing heart pulses, and more particularly, to a wristwatch having a first electric terminal on a bottom cover to permit a close contact with the wrist of one hand and a second electric terminal on the front side of the wristband for two fingers of another hand to touch thereon. Accordingly, the accuracy in measuring the heart pulse rate is reinforced.

2. Description of the Related Art

Generally, the heart pulses significantly varies during an exercise session. It is essential to monitor the heart pulse rate during the exercise session since the greatest benefit from exercise occurs when the heart pulse rate rises to 60% of the maximal rate. In exceeding this percentage, it will be harmful to the human body. Accordingly, to facilitate the measuring action and to provide accurate readings are important to the health during the exercise session.

Conventional heart pulse sensors are of various types and forms. U.S. Pat. No. 4,409,983, U.S. Pat. No. 4,224,948, U.S. Pat. No. 4,120,269 and U.S. Pat. No. 5,807,267 teach different kinds of pulse-sensing watches while the employed sensors are selected from the group consisting of infrared sensors, exhaust sensors, piezo pressure sensors, and optical sensors. Due to the influence of various external factors, the accuracy of the infrared sensor leaves much to be desired. As for the sensor detecting the voltage frequency change during blood circulation, the detection interface in contact with the human body has to be taken into account. If the detection interface is not able to ensure an effective contact with the human body, the measured heart pulse rate may be inaccurate. For example, in taking a metal surface as the detection interface, the contact will be unstable due to the slippery metal surface when the skin with perspiration is in contact with the interface. Accordingly, the accuracy will be seriously affected.

U.S. Pat. No. 5,807,267 teaches a heart pulse rate monitor assembly with sensor means mounted on a bottom side of a wristband for sensing heart pulses of the radial artery of the user. The assembly includes a piezo pressure sensor or an optical sensor adjacent to the radial artery for sensing the heart pulses thereof. The disadvantages thereof lie in that the measured result is easily influenced by external factors. Meanwhile, whether the detecting position is correct or not plays a significant part in the accurate readings. This apparatus may be suitable for medical professionals like physicians, nurses, etc. However, it is much difficult for normal persons to exactly locate the radial artery for an accurate detection of the heart pulses.

In addition to the convenient use, how to improve the sensing accuracy is also the main consideration of the invention.

SUMMARY OF THE INVENTION

It is a primary object of the invention to eliminate the aforementioned drawbacks and to provide a wristwatch with the function of sensing heart pulses having two conductive rubber strips on the surface of a wristband that are employed to be one electric terminal and has an antislip configuration for improving the accuracy in sensing the heart pulse rate.

It is another object of the invention to provide a wristwatch with the function of sensing heart pulses having another electric terminal on a bottom cover for contact with a first hand around which the wristwatch is worn. When fingers of a second hand touch the electric terminal consisting of conductive rubber strips, an electric connection between both electric terminals is created by both hands. The circulation of blood produces electric voltage, and different heart pulse rate will result in the change of voltage frequency. Besides, the farther is the blood, the more evidently the voltage frequency changes. If the right hand touches the second electric terminal and the first electric terminal is in contact with the left hand, the blood between the left and the right hand flows at a longest distance. Thus, the change of the voltage frequency between both electric terminals permits a more accurate detection of heart pulses.

BRIEF DESCRIPTION OF THE DRAWINGS

The accomplishment of this and other objects of the invention will become apparent from the following descriptions and its accompanying drawings of which.

DETAILED DESCRIPTION OF THE PREFERRED EMBODIMENT

Figure 1:
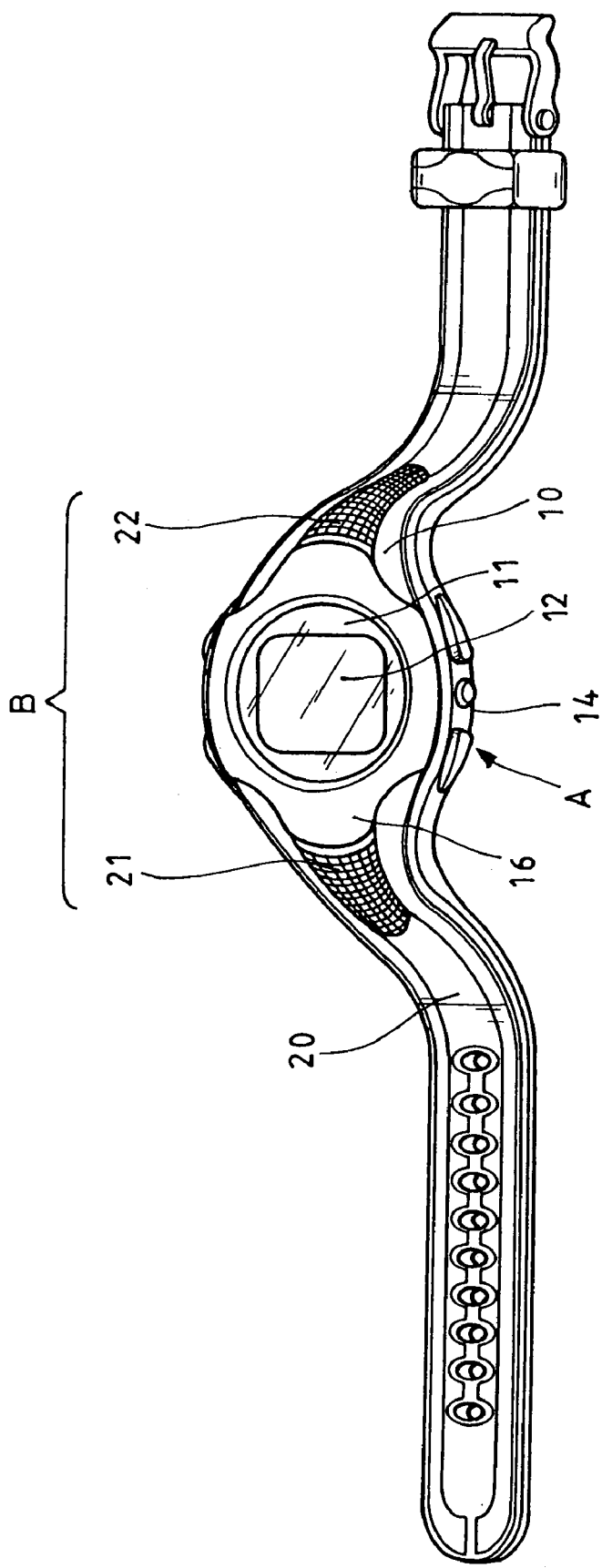
FIG. 1 is a perspective view of the invention.

First of all, referring to FIGS. 1 through 4, a wristwatch with the function of sensing heart pulses at least includes:

A watch housing 10 made of nonconductive material, the watch housing 10 having a crystal 11 at the front side thereof;

a liquid crystal display 12 positioned under the crystal 11 of the watch housing 10;

a voltage sensor 13 for detecting the voltage frequency change created by blood circulation within a human body, the voltage sensor having a plurality of components disposed on a circuit board 131 under the liquid crystal display 12;

a bottom cover 14 made of conductive material and positioned at the bottom side of the watch housing 10, at least a conducting connection element 15 being interposed between the bottom cover 14 and the circuit board 131 for creating an electric connection such that the bottom cover 14 serves as a first electric terminal A in close contact with the wrist of a first hand 30 of a watch wearer;

a wristband 20 made of nonconductive material and attached to both ends of the watch housing 10;

two conductive rubber strips 21, 22 positioned at the top of the wristband 20, the conductive rubber strips 21, 22 each having a conducting pin 211, 221 at both ends of the watch housing 10 for creating an electric connection between the conductive rubber strips 21, 22 and the circuit board 131 of the voltage sensor 13 such that the conductive rubber strips 21, 22 serves as a second electric terminal B to allow a stable contact with two fingers of a second hand of the watch wearer; and three inductors L1, L2, L3 disposed within the voltage sensor 13, the inductors L1, L2, L3 being coupled with both conductive rubber strips 21, 22 of the second electric terminal B and the bottom cover 14 of the first electric terminal A so that the measured voltage change frequency undergoes a static electric filtration by means of the inductors L1, L2, L3 and is transmitted to a filter shaping circuit 132 for creating signals that are brought into a central processing unit (CPU) 133 with an internal or an external amplifying circuit 134 and then amplified by the amplifying circuit 134 for central processing unit 133 to perform the processing and the calculating actions thereof, the processed result of the heart pulse rate in beats per minute being presented on the liquid crystal display 12.

The electronic components of the aforementioned filter circuit 132 and the amplifying circuit 134 belong to the prior art so that no further descriptions thereof are given hereinafter.

Figure 2:
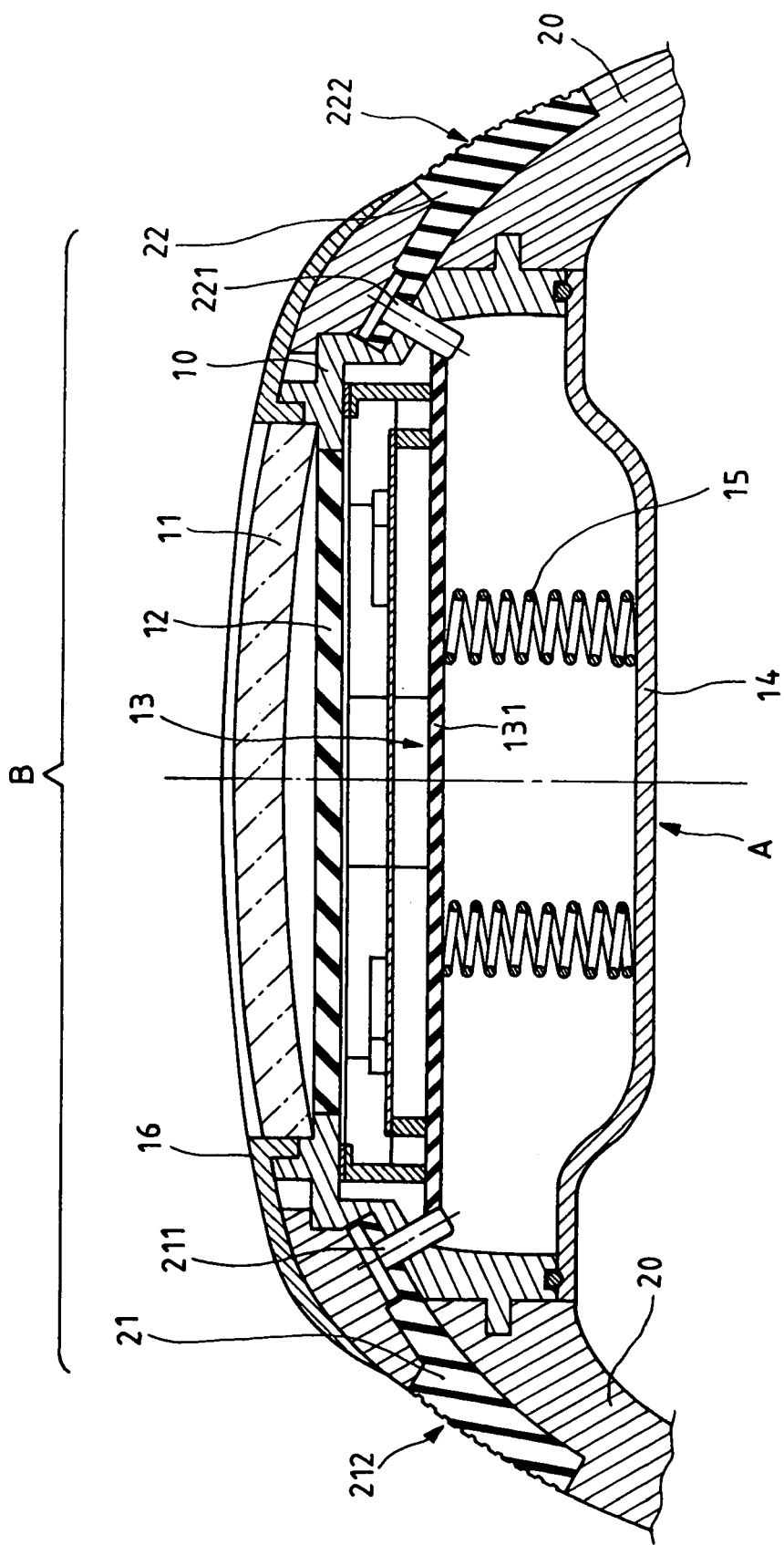
FIG. 2 is a longitudinal section of the invention.
Figure 3:
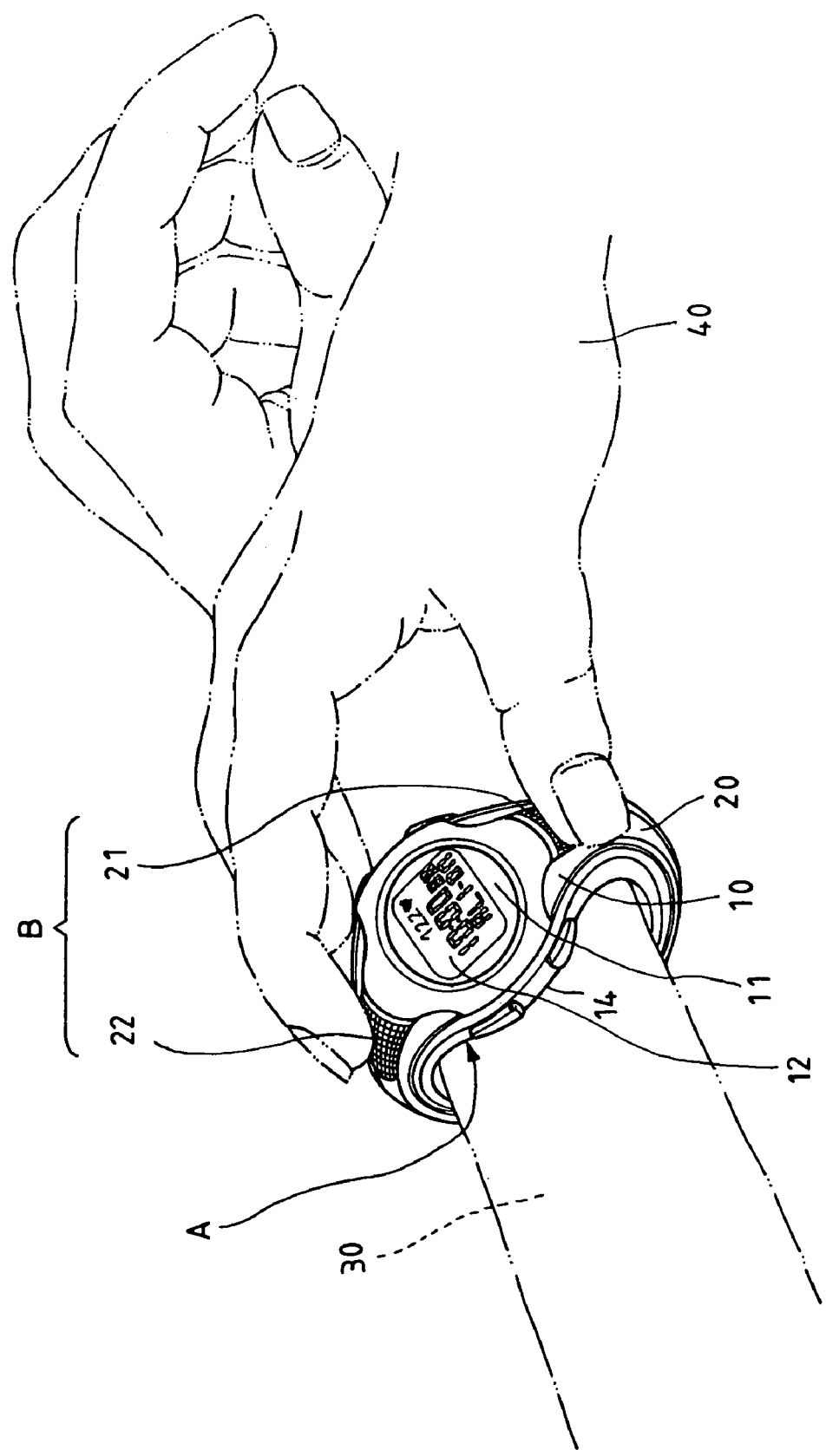
FIG. 3 is a perspective view of the invention, showing the use thereof.
Figure 4:
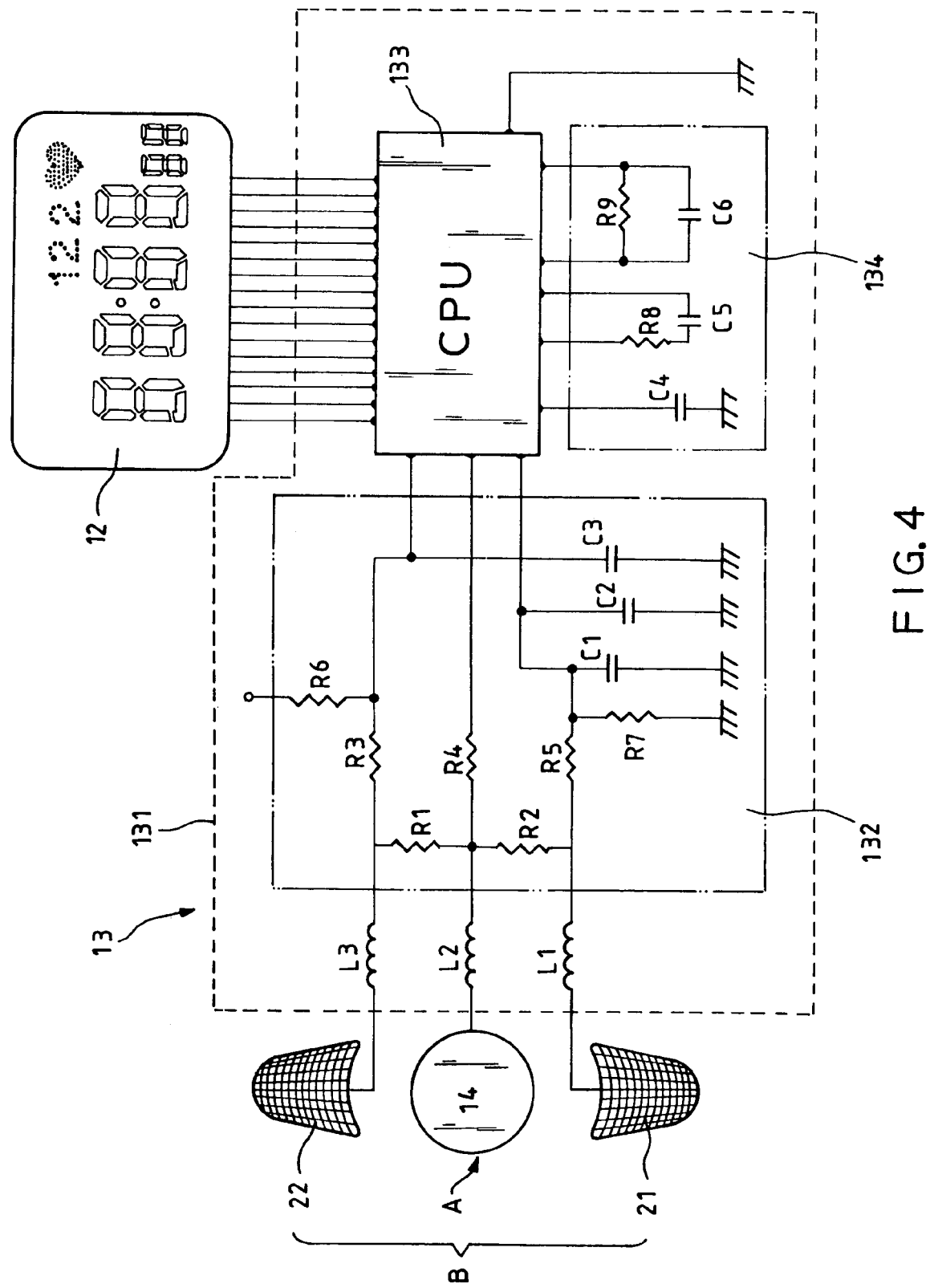
FIG. 4 is a circuit diagram of a voltage sensor of the invention.

Based on the above-mentioned configuration, the invention features the surface of the nonconductive wristband 20 on which two conductive rubber strips 21, 22 are mounted. The conductive rubber strips 21, 22 have excellent conductivity as metal, are kind to the skin, and avoid undesirable slip. As shown in FIG. 2, both conductive rubber strips 21, 22 have an antislip surface 212, 222 extended in a zigzag manner, thereby preventing both pressing fingers even with perspiration from slip (see FIG. 3). Accordingly, a more accurate detection of the voltage frequency change during blood circulation is ensured. Furthermore, an annular metal piece 16, as shown in FIGS. 1 and 2, is disposed around the crystal 11 for protecting the watch housing 10 against shock. However, the annular metal piece 16 may not be in contact with the conductive rubber strips 21, 22.

Again, referring to FIGS. 2 and 3, the first electric terminal A installed at the bottom cover 14 of the watch housing 10 touches the wrist portion of the left hand 30 in the ordinary state. Moreover, the whole surface of the bottom cover 14 is at the disposal of the first electric terminal A. When two fingers of the right hand 40 press against the conductive rubber strips 21, 22 of the second electric terminal B, respectively, the first electric terminal A will also be compressed in a close contact with the wrist of the left hand 30, thereby creating the electric connection between both electric terminals. Meanwhile, the circulation of blood produces electric voltage, and different heart pulse rate will result in the change of voltage frequency. Besides, the farther is the blood, the more evidently the voltage frequency changes. If the right hand 40 touches the second electric terminal B and the first electric terminal A is in contact with the left hand, the blood between the left and the right hand flows at a longest distance. Thus, the change of the voltage frequency between both electric terminals A, B can evidently occur for a more accurate detection of heart pulses.

Figure 5:
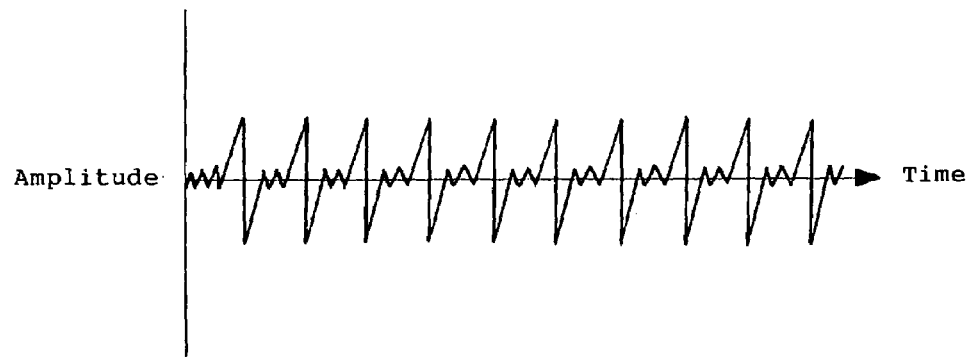
FIG. 5 is a diagram of the amplitude of the heart pulse signal.
Figure 6:
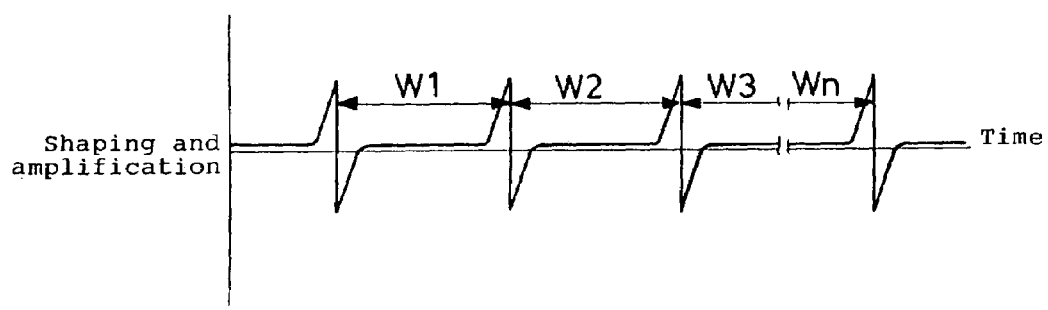
FIG. 6 is a diagram of the amplitude of the heart pulse signal after amplification.

Signals in dense fluctuation obtained from both electric terminals A, B are illustrated in FIG. 5. The signals shown in FIG. 6 are reshaped and amplified by the filter shaping circuit 132 and the amplifying circuit 134. Accordingly, the wave width W1, W2, W3, . . . Wn can be easily processed and calculated by central processing unit 133 for obtaining the heart pulses pro minute. The calculated result of the heart pulse rate in beats per minute can then be presented on the liquid crystal display 12.

In the invention, two sets of electric terminals A, B located at different positions are employed to accurately measure the heart pulse rate. The second electric terminal B consists of two conductive rubber strips 21, 22. As shown in FIG. 2, they are positioned at the front side of the insulation wristband 20. Since the watch housing 10 is also insulated, the conducting pins 211, 221 are employed to create the electric connection with the circuit board 131 of the voltage sensor 13. Meanwhile, the detecting accuracy can be increased by use of two pieces of conductive rubber strips 21, 22. In addition, the conductive rubber strips 21, 22 of the invention meets the requirement of practical use.

Many changes and modifications in the above-described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A wristwatch with the function of sensing heart pulses comprising:
   a) a watch housing made of nonconductive material, the watch housing having a crystal at the front side thereof;
   b) a liquid crystal display positioned under the crystal of the watch housing;
   c) a voltage sensor for detecting the voltage frequency change created by blood circulation within a human body, the voltage sensor having a plurality of components disposed on a circuit board under the liquid crystal display;
   d) a bottom cover made of conductive material and positioned at the bottom side of the watch housing, at least a conducting connection element being interposed between the bottom cover and the circuit board for creating an electric connection such that the bottom cover serves as a first electric terminal in close contact with the wrist of a first hand of a watch wearer;
   e) a wristband made of nonconductive material and attached to both ends of the watch housing;
   f) two conductive rubber strips positioned at the top of the wristband, the conductive rubber strips each having a conducting pin at both ends of the watch housing for creating an electric connection between the conductive rubber strips and the circuit board of the voltage sensor such that the conductive rubber strips serves as a second electric terminal to permit the contact with two fingers of a second hand of the watch wearer; and
   g) three inductors disposed within the voltage sensor, the inductors being coupled with both conductive rubber strips of the second electric terminal and the bottom cover of the first electric terminal so that the detected voltage change frequency undergoes a static electric filtration by means of the inductors and is transmitted to a filter shaping circuit for creating signals that are brought into a central processing unit with an internal or an external amplifying circuit and then amplified by the amplifying circuit for central processing unit to perform the processing and the calculating actions thereof whereby the processed result of the heart pulse rate in beats per minute can be presented on the liquid crystal display.

2. The wristwatch with the function of sensing heart pulses as recited in claim 1 wherein an annular metal piece is disposed around the crystal for protecting the watch housing against shock.

3. The wristwatch with the function of sensing heart pulses as recited in claim 1 wherein both conductive rubber strips have an antislip surface extended in a zigzag manner.

* * * * *